United States Patent [19]

Abramov et al.

[11] 4,117,244

[45] Sep. 26, 1978

[54] METHOD OF PRODUCING 2,6-DITERTBUTYL-4-METHYLPHENOL

[76] Inventors: Ivan Egorovich Abramov, prospekt Lenina, 87, kv. 15; Felix Borisovich Gershanov, prospekt Lenina, 81, kv. 6; Vladimir Romanovich Dolidze, ulitsa Kurchatova, 30, kv. 8, all of Bashkirskaya ASSR, Sterlitamak; Nina Vasilievna Zakharova; Alexandr Grigorievich Liakumovich, both of ulitsa Galeeva, 10, kv. 8, Kazan; Jury Ivanovich Michurov, prospekt Lenina, 13, kv. 4, Bashkirskaya ASSR, Sterlitamak; Vasily Dmitrievich Popov, Volochaevskaya ulitsa, 18a, kv. 15, Bashkirskaya ASSR, Sterlitamak; Grigory Iosifovich Rutman, ulitsa Revoljutsionnaya, 7, kv. 6, Bashkirskaya ASSR, Sterlitamak; Zoya Stepanovna Shalimova, ulitsa Druzhby, 19, kv. 56, Bashkirskaya ASSR, Sterlitamak, all of U.S.S.R.

[21] Appl. No.: 695,159

[22] Filed: Jun. 11, 1976

[51] Int. Cl.$^2$ .............................................. C07C 37/10
[52] U.S. Cl. .................................................... 568/799
[58] Field of Search ........... 260/624 R, 624 C, 621 D, 260/621 H, 621 M

[56] References Cited

U.S. PATENT DOCUMENTS 3,946,086  3/1976  Gershanov et al. ............. 260/624 R

FOREIGN PATENT DOCUMENTS 1,229,480  0000  United Kingdom ................ 260/624 R Primary Examiner—James O. Thomas, Jr.
Assistant Examiner—Werren B. Lone
Attorney, Agent, or Firm—Haseltine, Lake & Waters

[57] ABSTRACT

A method of producing 2,6-ditertbutyl-4-methylphenol comprises hydrogenolysis of N,N-dimethyl-(3,5-ditertbutyl-4-hydroxybenzyl)-amine in the presence of a fused catalyst, containing Ni, Al, Ti, in the medium of a solvent, namely 2,6-ditertbutyl-4-methylphenol solvent medium.

The invention allows improving the quality of the product and obtaining it with a high yield.

4 Claims, No Drawings

METHOD OF PRODUCING 2,6-DITERTBUTYL-4-METHYLPHENOL

The present invention relates to methods of producing 2,6-ditertibutyl-4-methylphenol.

2,6-Ditertbutyl-4-methylphenol is an effective stabilizer for various types of synthetic rubbers, it protects vulcanizates based on natural, butadiene-styrene, isoprene, butadiene, butadiene-nitrile and chloroprene rubbers from thermal aging and partly from light aging, and is also used in light and colored rubber articles. 2,6-Ditertbutyl-4-methylphenol is used as a thermal stabilizer of polyethylene and polypropylene fibers and is also an effective stabilizer of food products.

A method of producing 2,6-ditertbutyl-4-methylphenol by catalytic hydrogenolysis of N,N-dimethyl-(3,5-ditertbutyl-4-hydroxy-benzyl)-amine in an organic solvent medium is widely used in the art.

Particularly, a method of producing 2,6-ditertbutyl-4-methylphenol by hydrogenolysis of N,N-dimethyl-(3,5-ditertbutyl-4-hydroxy-benzyl)-amine in decalin in the presence of a catalyst, containing Ni, Al, Ti, is known in the art (British Pat. No. 1,229,480).

The disadvantage of this prior-art method resides in that during hydrogenolysis N,N-dimethyl-(3,5-ditertbutyl-4-hydroxybenzyl)-amine is partly resinified in decalin; the isolated 2,6-ditertbutyl-4-methylphenol contains about 5% of resinification products which impart a yellow color to it.

Besides, for isolation of 2,6-ditertbutyl-4-methylphenol from the reaction mixture, rectification of the reaction mixture and solvent recovery are required, making the process more complicated and expensive.

2,6-Ditertbutyl-4-methylphenol produced by said method can be used for food products only after a complicated purification process, e.g. by rectification or crystallization.

The object of the present invention is to improve the method of producing 2,6-ditertbutyl-4-methylphenol by catalytic hydrogenolysis of N,N-dimethyl-(3,5-ditertbutyl-4-hydroxybenzyl)-amine in order to simplify the technology of the process, to decrease the cost of the product and to improve its quality.

Said object has been acoomplished in a method of producing 2,6-ditertbutyl-4-methylphenol by catalytic hydrogenolysis of N,N-dimethyl-(3,5-ditertbutyl-4-hydroxy-benzyl)-amine in the presence of a fused catalyst containing nickel, aluminum and titanium in an organic solvent medium, wherein, according to the invention, 2,6-ditertbutyl-4-methylphenol is used as a solvent. The use of 2,6-ditertbutyl-4-methylphenol as a solvent allows simplifying the process of isolating 2,6-ditertbutyl-4-methylphenol from the reaction mixture by eliminating the rectification of the reaction mixture and solvent recovery.

Besides, during hydrogenolysis in the presence of 2,6-ditertbutyl-4-methylphenol secondary resinification processes are inhibited, this allowing the obtaining of 2,6-ditertbutyl-4-methylphenol of the required purity without complicated purification stages, and with a yield reaching 98.4%.

The resulting product is white, odorless, its melting point is 69.9°±0.1° C. and it meets the requirements of the food industry.

For a better understanding of the invention an example is presented hereinbelow.

EXAMPLE 1

The process is carried out in a glass reactor equipped with a thermometer, a Schott filter for better oxygen distribution, a coil for heating hydrogen and a reflux condenser The reactor is charged with 90.0 grams of a fused catalyst (of "Raney nickel" type containing 50% Ni, 45% Al and 5% Ti, grain size being 2–3 mm), 20 grams of 2,6-ditertbutyl-4-methylphenol, 20 grams of N,N-dimethyl-(3,5-ditertbutyl-4-hydroxybenzyl) - amine. The reactor temperature is 110° C., hydrogen flow rate is 25 ml/min., reaction time is 2 hours. When the reaction is over, the product is discharged from the reactor. 36.0 grams of a white, odorless crystalline product with a melting point of 69.9° C. are obtained. The yield of 2,6-ditertbutyl-4-methylphenol is 98.4% of theory. The quality of the obtained 2,6-ditertbutyl-4-methylphenol meets the requirements of the food industry.

What is claimed is:

1. In a method of producing 2,6-ditertbutyl-4-methylphenol which comprises hydrogenolysis of N,N-dimethyl-(3,5-ditertbutyl-4-hydroxy-benzyl)-amine in the presence of a fused catalyst containing Ni, Al, and Ti, in the medium of a solvent, the improvement comprising using 2,6-ditertbutyl-4-methylphenol as the solvent.

2. The method of claim 1 wherein the hydrogenolysis is carried out at a temperature of 110° C.

3. The method of claim 2 wherein the hydrogen flow rate is 25 ml/min.

4. The method of claim 3 wherein the catalyst consists of 50% Ni, 45% Al and 5% ti.

* * * * *